United States Patent
Tenkanen et al.

[11] Patent Number: 6,152,194
[45] Date of Patent: Nov. 28, 2000

[54] METHOD AND AN EQUIPMENT FOR PORTIONING LIQUID CONSIGNMENTS

[75] Inventors: Tuomas Tenkanen; Pekka Ronka, both of Espoo, Finland

[73] Assignee: Fluilogic Systems OY, Espoo, Finland

[21] Appl. No.: 09/284,177

[22] PCT Filed: Oct. 6, 1997

[86] PCT No.: PCT/FI97/00603

§ 371 Date: Apr. 8, 1999

§ 102(e) Date: Apr. 8, 1999

[87] PCT Pub. No.: WO98/15800

PCT Pub. Date: Apr. 16, 1998

[30] Foreign Application Priority Data

Oct. 8, 1996 [FI] Finland .................................. 964020

[51] Int. Cl.[7] .............................. G01F 11/00; B65B 3/30; B01L 3/02
[52] U.S. Cl. ............................ 141/130; 141/1; 422/400; 417/472
[58] Field of Search .................................. 222/1, 63, 207, 222/214, 333, 392; 141/1, 130; 417/472; 422/100

[56] References Cited

U.S. PATENT DOCUMENTS

| | | | |
|---|---|---|---|
| 4,047,851 | 9/1977 | Bender | 417/412 |
| 4,461,328 | 7/1984 | Kenney | 422/100 |
| 4,987,726 | 1/1991 | Petho et al. . | |
| 4,999,164 | 3/1991 | Puchinger et al. | 422/100 |
| 5,156,811 | 10/1992 | White | 422/100 |
| 5,364,595 | 11/1994 | Smith | 422/100 |
| 5,580,529 | 12/1996 | Devaughn et al. | 422/100 |
| 5,638,986 | 6/1997 | Tuominen et al. | 222/1 |

FOREIGN PATENT DOCUMENTS 94675 11/1992 Finland .

*Primary Examiner*—J. Casimer Jacyna
*Attorney, Agent, or Firm*—Ware, Fressola, Van Der Sluys & Adolphson LLP

[57] ABSTRACT

This invention relates to a method and an equipment for portioning of liquid consignments of specific amounts and to the packaging of these small liquid consignments in mass production. The portioning is executed with a bellows, which defines an air space of varying volume, that the air stream caused by the bellows establishes the injection and suction of a liquid. According to the invention the air space is connected to the suction tip (4), which holds a liquid space confined by a filter permeable to air stream but impermeable to liquid. When in the suction phase the liquid is sucked into the suction tip (4) by the motion of the liquid, and in the injection phase the reverse motion of the bellows is used in injecting the liquid consignment from the suction tip, and the injection of the liquid consignment of certain volume is based on a corresponding volume change in the air space of the bellows established by an equipment controlling the bellows. Serial portioning may take place so that a liquid volume of multiple times of the liquid consignments is sucked into the suction tip (4), after which the liquid consignments are portioned by the reversible motions of the bellows produced by the equipment controlling the bellows, which may be a step motor, for example. The suction tip may be removable, in which case the liquid to be portioned may be changed without having to clean the equipment, since the filter (17) in the suction tip prevents the contamination of the air space of the bellows.

18 Claims, 2 Drawing Sheets

METHOD AND AN EQUIPMENT FOR PORTIONING LIQUID CONSIGNMENTS

TECHNICAL FIELD

This invention relates to a method and an equipment for portioning liquid consignments of specific amounts. In addition, the invention comprises the use of the equipment in packaging of small liquid consignments.

BACKGROUND OF THE INVENTION

Liquids which are sold in small consignments, such as pharmaceutical products and reagents, have been packed in tubes, bottles, or other similar containers with an equipment, which automatically fills and closes the container and attaches an etiquette to it. On the packaging lines concerned, the liquid to be packed is typically led through a portioner or a part of the portioner, while the portioning space is full of the liquid concerned. Peristaltic pumps and rotating piston pumps, among others, have been used as portioners with liquid consignments of the magnitude of few milliliters.

The patent document U.S. Pat No. 4,987,726 features a certain packaging line of pharmaceutical liquids in accordance with the prior art, where the liquid, driven by the hydrostatic pressure, flows from an upper container to bottles which are preceding on the packaging line.

The above described technique is severely inadequate in the respect that, if the equipment is used in packaging several products, then due to the risk of contamination the portioning spaces and tubes have to be emptied and cleaned thoroughly every time a change is made from one product to the next. These difficult and time consuming manouvers present a serous impediment especially when the consignments are small, typically in the range of 100–5000 packages, and the product repertuare is diverse.

SUMMARY OF THE INVENTION

The objective of the invention is to establish a solution, which removes the disadvantages associated with cleaning problems in accordance with the prior art, and makes it possible to switch quickly from packaging or portioning one liquid to packaging or portioning the next liquid. The method in accordance with the invention is characterised by the portioning being executed with a bellows, which establishes the suction and the injection of the liquid with an air stream, and the air space defined by the bellows is in conjunction with a suction tip, which contains a liquid space limited by a filter permeable to the air stream but impermeable to the liquid, and when in suction phase the movement of the bellows is being used in sucking the liquid to the suction tip, and when in the injection phase an opposite movement of the bellows is being used in injecting the liquid consignment to be portioned from the suction tip, and the injection is being based on a change in volume of the air space of the bellows, corresponding to the volume of the liquid consignment, established by an equipment controlling the bellows.

The relevant advantage of the invention in comparison to the prior art is that, the liquid to be portioned is taken only in the suction tip, from which during portioning it is injected by a change of direction in the air stream. The suction tip may be a simple tube equipped with a filter, where the filter prevents the liquid from entering the bellows, while allowing the air stream of the bellows to pass through at the same time for establishing the suction and injection of the liquid. By this the contamination of the bellows acting as a portioner is prevented, and the need for cleaning the bellows ceases to exist.

With regards to the the equipment controlling the bellows, a reference is made to a former application FI 94675 of the applicant. In this document, which relates to the accurate portioning of small liquid batches, and where the bellows acts as a liquid filled portioning space, the establishment of small volume changes with a calibrated equipment such as a stepper motor, pietzorod or servomotor has been described in detail. In the case of the invention concerned, any special calibration is usually unnecessary, because while the bellows functions with air instead of liquid the accuracy of the portioning with liquid consignments of 1 milliliter or smaller is despite the calibration of the order of 1%. This is an adequate accuracy even in portioning of very expensive products, where an excess dose causes financial losses to the producer.

According to the invention the suction tip is preferably removable, and the filter it contains is a sterile aerosol filter, which is permeable to air stream but impermeable to liquid drops of any size. During portioning, the liquid to be portioned can be changed simply by changing the suction tip, which may happen in a couple of seconds. Since the suction tips are disposable, changing from one liquid to another requires no cleaning procedures.

In mass production, a volume multiples of any consignment or portion may be sucked into the suction tip. For example 5–20-fold volume may be portioned to a series of packages by volume changes established by sequential movements of the bellows. After the portioning sequence is over, the same suction tip may be filled again with the same liquid or the product may be changed by changing the suction tip.

According to the invention, the suction tip may be kept clean by blowing air with the bellows through the suction tip immediately before the sucking the liquid. In the intake of air of the bellows the suction tip comprising the filter is in place, and the filter prevents the contamination of the bellows. When the direction is reversed, the bellows begins to "flush" the suction tip clean air. The bellows and the suction tip are free of contamination, if the the tip is immersed in the liquid container every time during suction, and the air is being blown the same way every time inbetween the emptying of the suction tip and a new refill.

Very suitable liquids for portioning into packages in accordance with the invention are especially enzyme products, which have a high price and very small package size, preferably below 1 ml. The preferable amount to be sucked into the suction tip may be, for example, between 500–2000 microliters, from which for example 5–500 microliters, preferably 20–100 microliters are portioned per package. A 1000 microliter suction tip may be used, which is sucked to its full volume, and from which the liquid is portioned into 20 liquid packages of 50 microliters, which is appropriate, for example, for portioning of restriction enzymes into Eppendorf tubes.

The equipment in accordance to the invention and in accordance to the method described above comprise a bellows, which facilitates injection and suction by its reversible movements. The equipment is characterised by the bellows defining an air space, which is in conjunction with a suction tip, which has liquid space limited by a filter permeable to air stream but impermeable to liquid, and to this liquid space the liquid to be portioned may be sucked or injected, and that the bellows is in conjunction to the equipment controlling it, which establishes a volume change in the airspace of the bellows corresponding to the size of the liquid consignment.

The air space of the bellows, the volume of which changes the portioning, is preferably based the inside of the bellows, even though it may be an external space surrounding the bellows as well. The air space may be in connection to the suction tip through an air hose, which is preferably removable. The suction tip may be a simple tube, equipped with a an aerosol filter impermeable to liquid, and it may be adjoinable to the said air hose by pushing the ends of these two pieces so that they overlap and are squeezed to attach to each other.

The equipment controlling the bellows is preferably a stepper motor whose rotatory motion is transformable to linear motion which changes the volume of the bellows, for example by a pullable string or a band. The string or the band may be joined to the end of the bellows directly or through a lever mechanism. The sequential steps of the stepper motor, which produce a series of essentially uniform consignments from the liquid sucked into the suction tip, may be empirically determined. Instead of the steeper motor the equipment may be a pietzorod or a servomotor, which while connected to the end of the bellows produces the linear motion directly, without any transmission mechanism.

The invention further comprises the use of the above described equipment in packaging of small liquid consignments in mass production. This concerns especially enzyme products, which typically have a package size of 20–500 microliters.

BRIEF DESCRIPTION OF THE DRAWINGS

The invention is explained in more detail with examples with reference to the following drawings, of which, FIG. 1 schematically represents a portioning equipment according to the invention, where the suction and the injection are established with a bellows, which is moved by a stepper motor with the help of a lever and a pullable band rotatable around the axle of the motor.

BEST MODE FOR CARRYING OUT THE INVENTION

Figure 1:
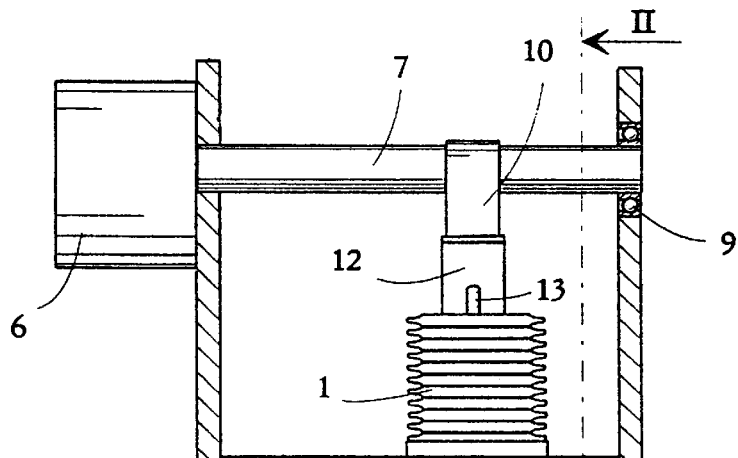
Figure 2:
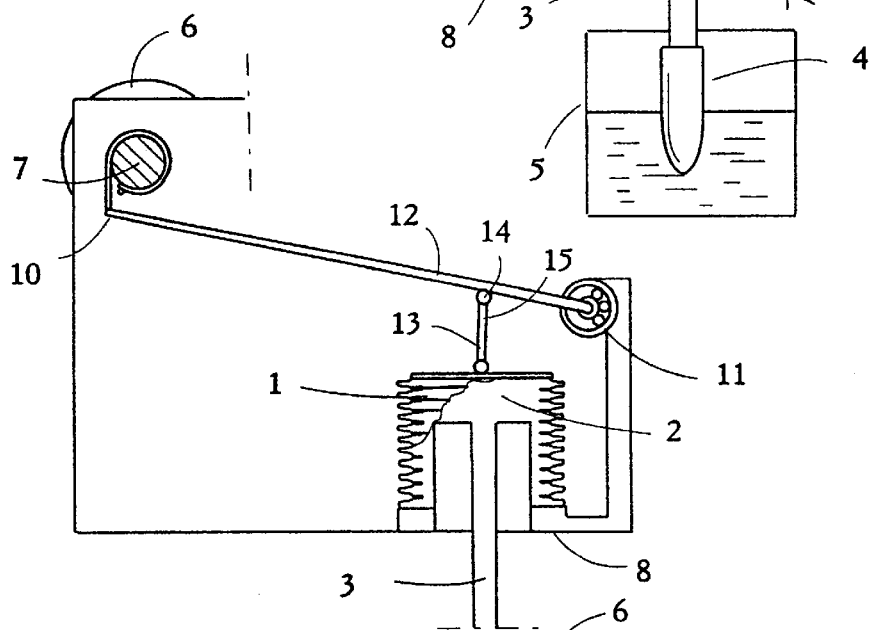
FIG. 2 represents an equipment at accordance with the FIG. 1 in the beginning of the injection phase seen from the view II—II.
Figure 3:
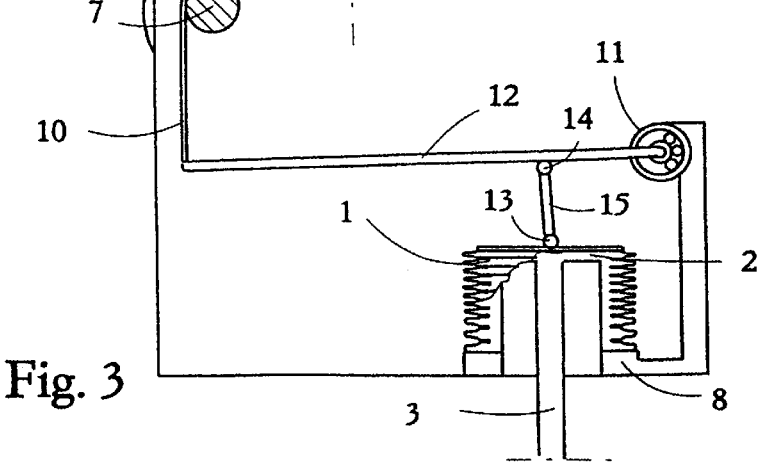
FIG. 3 represents an equipment in accordance with FIG. 2, but at the end of the injection phase.

The portioning equipment in accordance with FIGS. 1–3 comprises a flexible, reversibly movable bellows 1 made of rubber or metal, and an internal air space 2 which establishes the portioning by its volume changes. The air space 2 of the bellows is connected to the removable suction tip 4 via the air channel 3. The suction of the liquid from cuvette 5 or from some other source is established by stretching the bellows 1 so, that the volume of internal air space 2 grows. Correspondingly, the injection happens during the compression of the bellows 1 so, that the internal air space 2 contracts.

The motion of bellows 1 is facilitated by the rotatory axle 7, which is used by the stepper motor 6. The bottom of the bellows 1 is, as seen in FIG. 1, rigidly attached to the support structure 8, which supports the stepper motor 6 and its axles 7 as well. The end of the axle 7 is supported to the support structure 8 by the ball bearing 9. A pullable band 10 is attached to the axle 7, and the pullable band 10 is arranged to wind around the axle as represented in FIG. 2. The end of the pullable band 10 is attached to the lever 12 mounted to the support structure 8 with the ball bearing 11, and the lever 12 is attached to the bellows 1 via the joint lever 15 attached to its ends 13 and 14. The end of the bellows 1 thereby follows the mainly vertical motion of the lever 12 and pullable band 10 established by the rotation of the axle 7. This motion establishes the volume change of the air space 2 of the bellows 1 and thereby facilitates the injection or suction of a corresponding liquid consignment via the suction tip 4. In FIG. 2 the bellows 1 is in the initiation point of the portioning sequence, where the air space 2 of the bellows 1 is stretched to its maximum position, and the FIG. 3 shows end point of the portioning sequence, where the air space is contracted to a minimum. The contraction may be based on the spring force of the bellows 1, but also an additional spring (not featured here) may be used to help the bellows to contract.

Figure 4:
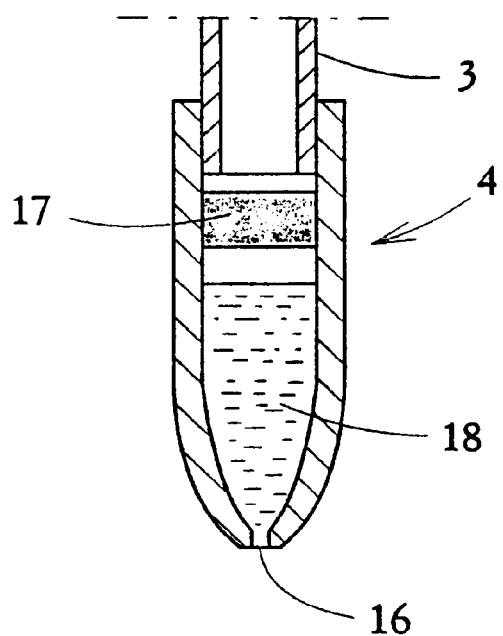
FIG. 4 represents a cut view of the suction tip of the equipment of FIGS. 1–3 in a larger scale.

The suction tip 4 at the end of the suction channel 3 comprises, according to FIG. 4, a narrowing tube, open from its tip 16, and the tube holds a firmly set aerosol filter, so, that there is a liquid space 18 between the tip 16 and the filter 17, to which the liquid to be portioned may be sucked. The aerosol filter 17 is permeable to a suction air stream, but holds all solid or liquid material or drops, and thereby prevents the contamination of the air channel 3 and the air space 2 of the bellows 1 by the liquid.

Figure 5:
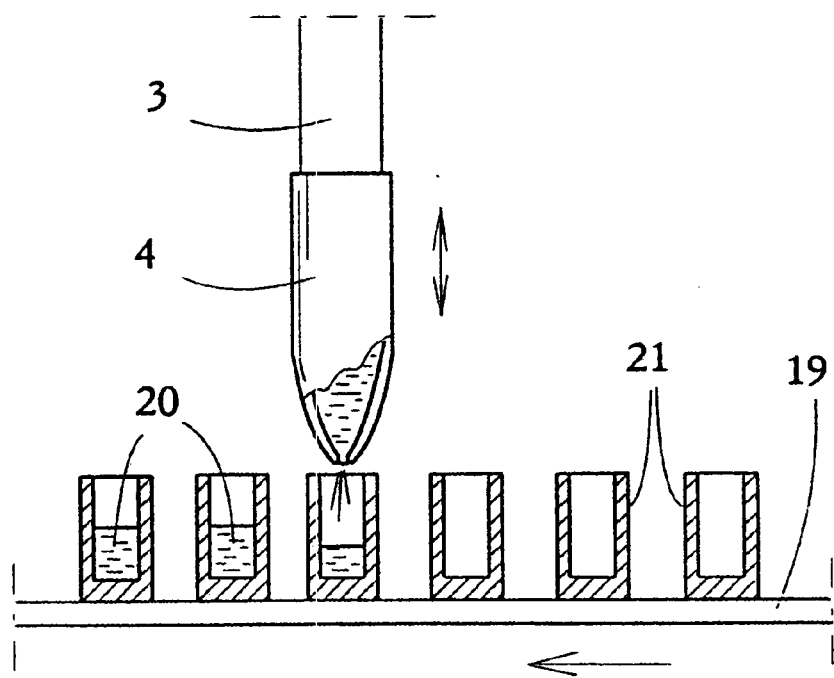
FIG. 5 represents portioning of liquid into packages preceding on a production line with the suction tip in accordance with FIG. 4.

FIG. 5 schematically represents the packaging line 19, with which using the suction tip 4 of FIG. 4, different liquid consignments 20 are portioned into packaging containers 21. The containers 21 one at a time pass by the suction tip 4, which fills each container with a liquid injected from the space 18, and the injection is based on the contraction of the bellows 1, which results in a volume change in air space 2.

In FIG. 2 the lever 12 used by the pacemotor is in its top position, when the volume of the air space 2 of the bellows is a maximum. In this initial position of portioning, the liquid space 18 of the suction tip 4 is filled by the liquid sucked from the cuvette 5. The portioning is then facilitated by the stepper motor 6, when the axle 7 of FIG. 2 rotates anti-clockwise, and when the pullable band 10 is released from the axle and lets the bellows contract along with its spring force, a liquid volume corresponding to the contraction of the airspace 2 is injected from the suction tip 4. After the injection the stepper motor 6 stops and starts again, when the rotation of the axle 7 produces the next portion, where essentially the same liquid volume is injected from the suction tip 4. This is continued, until a situation in accordance with FIG. 3 is met, where the liquid sucked into the liquid space 18 of the suction tip 4 has essentially been finished. If the volume of the liquid space 18 is of the order of 1 ml, for example, it is adequate for twenty liquid consignments of 50 microliter each without a refill. In practice the suction tip is not completely emptied, but after a portioning sequence the liquid space 18 of the tip 4 still holds some leftover liquid, which is injected to the cuvette 5 before a new refill. The refill is carried out by pacing the stepper motor to the opposite direction as in the case of portioning, when the pullable band 10 stretches the bellows 1 and the expansion of the air space 2 sucks liquid from cuvette 5 to the suction tip, after which the portioning may continue. Alternatively it is possible to change the liquid to be portioned, in which case the suction tip 4 at the end of the air channel 3 is replaced by another. Because the aerosol-filter 17 of the suction tip 4 has protected the bellows 1 and the air channel 3 from contamination, they need not be cleaned when the liquid is changed.

The portioning accuracy of the equipment was tested with portion sets of ten consecutive samples in different temperatures. The liquid to be portioned was a 50% glycerol solution, and a suction tip of 1 ml was used in portioning, which had the suction rate of 600 microliters/second and injection rate of 500 microliters/-second. The bellows used was a 2 ml nickel bellows, which was connected with a lever to a pullable string of polymer material wound around the axle of the stepper motor (Tamagava, 400 step) with a transmission ratio of 5:1 (the ratio of the motion of the string and the motion of the end of the bellows). The portion size was of the order of 50 microliters and the delay between consecutive portions was 1 s. The temperature of the first portioning set was −31 degrees Celsius, and the portion sizes in microliters were 54.1, 54.1, 53.1, 53.3, 53.3, 53.2, 53.0, 52.9, and 52.9. The average portion size is thereby 53.7 microliters with a standard deviation of 0.7 microliters.

The following table displays the results of the corresponding measurement sets in different temperatures.

TABLE

| Temperature (° C.) | Average portion size ($\mu$l) | STD ($\mu$l) |
| --- | --- | --- |
| −13 | 53.7 | 0.7 |
| −12 | 53.3 | 0.5 |
| −11 | 53.4 | 0.6 |
| −10 | 53.3 | 0.7 |
| −8 | 53.2 | 0.5 |
| −7 | 53.2 | 0.3 |
| −4 | 52.9 | 0.4 |
| −3 | 53.2 | 0.6 |
| +2 | 53.4 | 0.5 |

It is obvious to one skilled in the art, that the applications of the invention are not restricted to the examples represented, but may vary within the scope defined by the following patent claims. It is possible to construct a bellows so that the air space of varying volume lined by it is on the outside of the bellows. The form of the lever moving the bellows may vary, and it may be coupled with pullable band or bands to the axle of the pacemotor that the motor moves the bellows to both directions, i.e. both compresses and stretches it, regardless of the spring force of the bellows. As a substitute to the pullable band winding around the axle, an eccentric axle wound by the motor and coupled to the end of the bellows may be used. Alternatively the stepper motor may be replaced by a servomotor or a pietzorod, which may be coupled to the end of the bellows without any transmission mechanisms.

What is claimed is:

1. A method for producing portions of liquid (20) by use of a suction tip (4) containing a liquid space (18) confined by a filter (17) permeable to an air stream but impermeable to said liquid and a bellows (1) defining an air space (2) connected through an air channel (3) to said suction tip, the method comprising drawing liquid to said suction tip by means of a movement of the bellows, and injecting said liquid from the suction tip by means of reversed movement of the bellows, characterized in that a plurality of liquid portions (20) of a specified size are produced in a series operation which comprises the steps of drawing an amount of liquid to the suction tip (4), said amount being a multiple of an individual portion (20) to be produced, and then injecting said portions one by one at a number of subsequent injection steps, by use of an actuator (6) producing sequential movements of the bellows each with a change of the volume of said air space (2) corresponding to the size of the liquid portion that is injected and wherein the suction tip (4) is cleaned by letting the bellows (1) blow air through it immediately before the suction of the liquid to the suction tip (4).

2. A method in accordance with claim 1, characterised in that the suction tip (4) is removable and holds a filter (17), which is a sterile aerosol filter, which is permeable to air stream but holds liquid drops.

3. A method in accordance with claim 2, characterized in that the actuator is a stepper motor (6) that is producing reversible movements of the bellows (1).

4. A method in accordance with claim 3, characterised in that the suction tip (4) is cleaned by letting the bellows (1) blow air through it immediately before the suction of the liquid to the suction tip.

5. A method in accordance with claim 4, characterised in that the method is used in portioning different liquids by changing the removable suction tip (4) in between portionings.

6. A method in accordance with claim 5, characterised in that the method is used in portioning of a liquid, such as an enzyme product, into packages (21).

7. A method in accordance with the claim 6, characterised in that the liquid volume sucked into the suction tip is approximately 500–2000 microliters.

8. A method in accordance with claim 6, characterised in that the quantity of liquid (20) to be portioned per package (21) is of the order of 5–500 microliters, preferably approximately 20–100 microliters.

9. A method in accordance with claim 1, characterized in that the actuator is a stepper motor (6) that is producing reversible movements of the bellows (1).

10. A method in accordance with claim 1, characterised in that the method is used in portioning different liquids by changing the removable suction tip (4) in between portionings.

11. A method in accordance with claim 1, characterised in that the method is used in portioning of a liquid enzyme product into packages (21).

12. An equipment for producing portions of liquid (20) comprising a suction tip (4) containing a liquid space (18) confined by a filter (17) permeable to an air stream but impermeable to liquid, and a bellows (1) defining an air space (2) connected through an air channel (3) to said suction tip, to let liquid be drawn to the suction tip and injected from the same by means of reversible movements of the bellows, characterized in that the bellows (1) is connected to an actuator (6) adapted for production of a series of movements of the bellows so as to sequentially diminish the volume of said air space (2) and cause a series of liquid portions (20) to be injected one by one from the suction tip (4) wherein the suction tip (4) is structured to be cleaned using the bellows (1) to blow air through the suction tip (4) immediately before the suction of the liquid to the suction tip (4).

13. An equipment in accordance with the claim 12, characterised in that the suction tip (4) is removable and it comprises a filter (17), which is a sterile aerosol filter, which is permeable to air stream but impermeable to liquid drops.

14. An equipment in accordance with the claim 13, characterised in that the interior (2) of the bellows (1) is connected to the removable suction tip (4) via the air channel (3).

15. An equipment in accordance with claim 14, characterised in that the equipment controlling the bellows (1) is a stepper motor (6), the rotatory motion of an axle (7) used by the stepper motor being converted to a linear motion of the bellows (1).

16. An equipment in accordance with the claim 15, characterised in that the means for converting the motion is a pullable string or band woundable around the axle (7) of the motor (6).

17. The use of an equipment in accordance with the claim 12 in portioning of small quantities of liquid (20) into packages (21) in series production.

18. An equipment in accordance with claim 12, characterised in that the equipment controlling the bellows (1) is a stepper motor (6), the rotatory motion of an axle (7) used by the stepper motor being converted to a linear motion of the bellows (1).

* * * * *

UNITED STATES PATENT AND TRADEMARK OFFICE
CERTIFICATE OF CORRECTION

PATENT NO.    : 6,152,194
DATED         : November 28, 2000
INVENTOR(S)   : Tenkanen et al.

It is certified that error appears in the above-identified patent and that said Letters Patent is hereby corrected as shown below:

<u>Title page,</u>
Item [57], ABSTRACT,
Line 5, prior to "that" please insert -- so --.

<u>Column 2,</u>
Line 27, please delete "multiples" and substitute -- multiple -- therefor.

<u>Column 3,</u>
Line 4, after "based" please insert -- on --.
Line 22, please delete "steeper" and substitute -- stepper -- therefor.
Line 40, please delete "at" and substitute -- in -- therefor.
Line 41, please delete "in" and substitute -- at -- therefor.

<u>Column 4,</u>
Line 17, please delete "the".
Line 18, after "shows" please insert -- the --.

<u>Column 5,</u>
Line 18, please delete "31" and substitute -- 13 -- therefor.
Line 42, after "so" please insert -- , --.
Line 45, after "pacemotor" please insert -- so --.
Line 46, please delete "to" and substitute -- in -- therefor.

Signed and Sealed this

Twenty-seventh Day of April, 2004

JON W. DUDAS
*Acting Director of the United States Patent and Trademark Office*